(12) United States Patent
Shimoda (10) Patent No.: US 6,650,410 B2
(45) Date of Patent: Nov. 18, 2003

(54) APPARATUS, SYSTEM AND METHOD FOR CHECKING FILM FOR DEFECTS

(75) Inventor: Kazuhiro Shimoda, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 53 days.

(21) Appl. No.: 09/800,473

(22) Filed: Mar. 8, 2001

(65) Prior Publication Data

US 2001/0021016 A1 Sep. 13, 2001

(30) Foreign Application Priority Data

Mar. 8, 2000 (JP) ........................................ 2000-063027

(51) Int. Cl.[7] .............................................. G01N 21/00
(52) U.S. Cl. .................................................... 356/239.1
(58) Field of Search .............................. 356/239.1, 364, 356/365, 369; 349/117–120

(56) References Cited

U.S. PATENT DOCUMENTS

| | | | | |
|---|---|---|---|---|
| 5,311,340 A | * | 5/1994 | Murata et al. | 349/118 |
| 5,767,937 A | * | 6/1998 | Sumiyoshi | 349/117 |
| 5,948,487 A | * | 9/1999 | Sahouani et al. | 252/299.01 |
| 6,034,754 A | * | 3/2000 | Sato et al. | 349/102 |

FOREIGN PATENT DOCUMENTS

| | | | |
|---|---|---|---|
| JP | 6-214116 | 8/1994 | G02B/5/30 |

* cited by examiner

*Primary Examiner*—Michael G. Lee
*Assistant Examiner*—Jamara A Franklin
(74) *Attorney, Agent, or Firm*—Sughrue Mion, PLLC (57) ABSTRACT

An apparatus for checking a film for defects having a pair of polarizers placed on the opposite sides of the film to be checked, an illumination light source placed outside the pair of polarizers, a light receiving device placed outside the pair of polarizers and opposite from the illumination light source, and a correction film having substantially the same birefringent characteristics as a portion of the film to be checked having no optical defects. A direction in which the correction film is to be positioned is previously set according to the birefringent characteristics of the film to be checked. The correction film is placed between one of the pair of polarizers and the film to be checked. A luminance signal of light emits from the illumination light source, transmits through the film to be checked, the correction film and the pair of polarizers and is then obtained by the light receiving device to check the film for optical defects.

13 Claims, 7 Drawing Sheets

APPARATUS, SYSTEM AND METHOD FOR CHECKING FILM FOR DEFECTS

BACKGROUND OF THE INVENTION

1. Field of the Invention

The present invention relates to an apparatus, system and method for checking film for defects in a viewing angle widening film by using a simpler and easier process of optically checking the film for defects, and particularly for continuously checking the film in the process of manufacturing a viewing angle improving film for use in a liquid crystal display device or the like.

2. Description of the Related Art

Today, thin-film transistor (TFT) liquid crystal display devices and double supertwisted nematic liquid crystal (DSTN) display devices are being widely used as liquid crystal display devices. These liquid crystal display devices have a viewable region dependent on the viewing angle, and the display screen cannot be suitably viewed along a line out of the viewable region. For example, when the viewing angle is inclined up and down in a vertical direction, the color of the entire display screen becomes lighter and the contrast is lowered, or gray-scale inversion of a black display portion occurs to considerably reduce the viewability. In the case of large-screen liquid crystal display devices, such a contrast reduction or gray-scale inversion occurs more easily since the viewing angle is widened along with the increase in the area of the display screen. Therefore, there is a demand for a liquid crystal display device having a wide viewable region.

Under these circumstances, various means exist for improving viewing angle characteristics of liquid crystal display devices, e.g., a method of performing divided liquid crystal orientation in a liquid crystal display device, and a phase-difference film used as an optical compensation film that has a negative birefringence index have been studied.

For example, Japanese Patent Application Laid-open No. 6-214116 of the invention filed by the applicant of the present invention discloses an optical anisotropic element and a method of manufacturing the optical anisotropic element. According to the description in the publication, since liquid crystal molecules in liquid crystal cells of a liquid crystal display device are slightly tilted relative to the substrate of the liquid crystal display device when a voltage is applied, the liquid crystal display device can be regarded as a positive uniaxial optical anisotropic element having an optical axis in a direction slightly tilted relative to the substrate of the liquid crystal display device. Accordingly, it is possible to obtain a favorable liquid crystal display device having no viewing angle dependence by slightly tilting the optical axis of a negative uniaxial optical anisotropic element according to the above-mentioned tilt and compensating the phase difference caused by the liquid crystal cells with a phase difference caused by the optical anisotropic element. Based on this principle, the Applicant of the present invention manufactures a film which forms the optical anisotropic element as a wide view film for improving the angle at which a liquid crystal display device may be viewed.

To uniformly maintain liquid crystal cells in an optimized compensated state, a high degree of uniformity is required of the above-described liquid crystal viewing angle improving film constituted of a low-molecular liquid crystal and forming an optical anisotropic element. However, the above-described liquid crystal viewing angle improving film is manufactured through various complicated steps, including application of a liquid crystal to a flexible supporting member, drying, orientation and hardening of film. Therefore, there is a possibility of mixing and adhesion of foreign materials in and to the liquid crystal material to variously or randomly disorder the orientation of molecules of the low-molecular liquid crystal, and there is also a possibility of application non-uniformity causing variation in retardation value, resulting in generation of various defective portions which do not have the desired optical characteristics.

It is desirable that all of such defective portions be detected with accuracy in a manufacturing line for obtaining the above-described liquid crystal viewing angle improving film through a complicated manufacturing process, and that no liquid crystal viewing angle improving film having such defective portions be put on the market.

As a method for detecting defects in liquid crystal viewing angle improving films in a state of being conveyed in a manufacturing line, a method has been used in which the liquid crystal viewing angle improving film is interposed between a pair of polarizers one of which has, on one side of the liquid crystal viewing angle improving film, a polarizing transmission axis parallel to the direction of conveyance of the film, and the other of which has, on the other side, a polarizing transmission axis perpendicular to the direction of conveyance of the film, i.e., a pair of polarizers placed as crossed Nicols; detecting illumination light is projected from the outside of one of the pair of polarizers to the liquid crystal viewing angle improving film; transmitted light emergent from the opposite side is received with a line sensor or the like to obtain a signal representing the luminance of the transmitted light; and the luminance signal is processed by, for example, mathematical differentiation to detect a defective portion in the film surface according to a change in the luminance signal.

This method, however, entails a problem described below. When a luminance signal obtained by imaging with a charge-coupled device (CCD) camera or the like is displayed so as to form an image, a defective portion forms a brighter image portion in contrast with the background normal portion. However, the quantity of light transmitted through the normal portion is nonuniform because of the viewing angle dependence of the liquid crystal viewing angle improving film itself. Therefore, the signal-to-noise ratio of the luminance signal of the brighter image portion corresponding to the defective portion is low and the defective detection accuracy is low. Further, a nonuniform background portion in the normal portion may be removed by shading correction calculation. However, since the information in the luminance signal is also processed by the calculation, this method is not effective in improving the detection accuracy.

The above-described detection method makes it comparatively easy to detect defective portions by placing as crossed Nicols a pair of polarizers on the opposite sides of the liquid crystal viewing angle improving film with one of their polarizing transmission axes set parallel to the direction of conveyance of the film. Since the orientation of the liquid crystal in the liquid crystal viewing angle improving film is generally perpendicular to the polarizing transmission axis, the quantity of light transmitted through the surface of the normal film is small. However, the quantity of light transmitted through defective portions that form a brighter image region is also generally small, so that the signal-to-noise ratio of the luminance signal corresponding to defective portions is low and the defective detection accuracy is low.

Also, in the above-described method, a check of the film for defects in a liquid crystal viewing angle improving film in a state of being conveyed is made by using a line sensor having solid-state image pickup elements arranged in a row in a direction perpendicular to the direction of conveyance. Defects which appear continuously or periodically parallel to the arrangement of the solid-state image pickup elements, e.g., a stepped nonuniformity in a direction of the film thickness resulting from application nonuniformity, cannot be accurately detected from a change in the luminance signal obtained by the above-described line sensor.

Accordingly, it is not possible to accurately and reliably detect all defects caused during the manufacturing process.

This is not only a problem of the liquid crystal viewing angle improving film but also a problem common to all phase-different films utilizing any type of birefringence index.

SUMMARY OF THE INVENTION

In view of the above-described problem, an object of the present invention is to provide an apparatus, system and method for checking a film for defects in a manufacturing line or the like by using a simpler and easier process of optically detecting defects in the film, such that all optical defects caused during the manufacturing process can be accurately detected without any fail to be detected, and particularly to provide a film defect detecting system for making a continuous check of a film for defects due to mixing of a foreign material, orientation nonuniformity, stepped nonuniformity, etc., in the process of manufacturing a viewing angle improving film for use in a liquid crystal display or the like to accurately detect all of such defects without any fail.

To achieve the above-described object, according to one aspect of the present invention, there is provided an apparatus for checking a film for optical defects, comprising a pair of polarizers placed on opposite sides of a film surface of a film to be checked with respect to optical defects, the polarizers being parallel to the film, an illumination light source placed outside the pair of polarizers, the illumination light source projecting light onto the film through: a first polarizer of the pair of polarizers, light receiving unit placed outside the pair of polarizers and opposite from a placed position of the illumination light source, the light receiving unit receiving light transmitted through a second polarizer of the polarizers, and a correction film having substantially the same birefringent characteristics as a portion of the film having no optical defects, a direction in which the correction film is to be positioned being previously set according to the birefringent characteristics of the film, the correction film being placed in one of two spaces between the pair of polarizers and the film parallel to the film, characterized in that the luminance signal of light transmitted through the film, the correction film and the pair of polarizers is obtained by a light receiving unit to check the film for optical defects.

In the above-described apparatus, a portion of the film having no optical defects may be placed as the correction film after being rotated through 180 degrees along a plane corresponding to the film surface or after being reversed from front side to back side. Also, the correction film may be adhered to one of the pair of polarizers.

Preferably, the apparatus has an optical system for converging transmitted light on the light receiving unit, the optical system being provided in an optical path for the transmitted light between the light receiving unit and the second polarizer.

The light receiving unit may include solid-state image pickup elements, or other well-known image pickup elements. When the film is checked for optical defect during conveyance of the film, the light receiving unit comprises a plurality of solid-state image pickup elements arranged in a row inclined relative to a direction perpendicular to a direction of conveyance of the film.

Preferably, the pair of polarizers are placed in crossed-Nicols relationship with each other.

According to another aspect of the present invention, there is provided a film defect check system for checking a film continuously conveyed for optical defect, the system comprising a plurality of film defect checking apparatuses placed in a path through which the film is conveyed, each of the film defect checking apparatus having a pair of polarizers placed on opposite sides of a film surface of the film to be checked with respect to optical defects, the polarizers being parallel to the film, an illumination light source placed outside the pair of polarizers, the illumination light source projecting light onto the film through a first polarizers of the pair of polarizers, light receiving unit placed outside the pair of polarizers and opposite from a placed position of the illumination light source, the light receiving unit receiving light transmitted through a second polarizer of the polarizers, and a correction film having substantially the same birefringent characteristics as a portion of the film having no optical defects, a direction in which the correction film is to be positioned being previously set according to the birefringent characteristics of the film, the correction film being placed in one of two spaces between the pair of polarizers and the film parallel to the film, characterized in that directions of polarizing transmission axes of the pairs of polarizers of the plurality of film defect checking apparatuses are respectively set at different angles from a direction of conveyance of the film continuously conveyed.

Preferably, in the above-described system, a number of the film defect checking apparatuses is at least three, and the pairs of polarizers of the at least three film defect checking apparatuses are placed so that the angles each of which is an angle of intersection of one of the pair of polarizers in each of film defect checking apparatuses and a phase-delay axis of a portion of the film having no optical defects include an angle of about zero, an angle in a range of 5 to 15 degrees, and an angle in a range of 35 to 45 degrees.

Preferably, in at least one of the film defect checking apparatuses, the light receiving unit comprises a plurality of solid-state image pickup elements arranged in a row inclined relative to a direction perpendicular to the direction of conveyance of the film.

Preferably, the pair of polarizers are placed in crossed-Nicols relationship with each other.

According to still another aspect of the present invention, there is provided a method of checking a film for defects, in which a film interposed between a pair of polarizers parallel to each of the pair of[]polarizers is checked for optical defects by projecting illumination light from the outside of a first polarizer of the pair of polarizers, and by receiving light transmitted through a second polarizer of the polarizers, the method comprising the steps of placing a correction film which has substantially the same birefringent characteristics as a portion of the film having no optical defects in one of two spaces between the pair of polarizers and the film parallel to the film surface of the film, and a direction in which the correction film is to be positioned being previously set according to the birefringent characteristics of the film, and projecting the illumination light to the first polarizer.

directions of polarizing transmission axes of the pair of polarizers are set according to respective types of defects in the film, the pair of polarizers keeping crossed-Nicols relationship with each other.

DESCRIPTION OF THE PREFERRED EMBODIMENTS

Film defect checking apparatuses (apparatuses for checking film for defects) will be described with preferred embodiments of the present invention with reference to the accompanying drawings.

Figure 1:
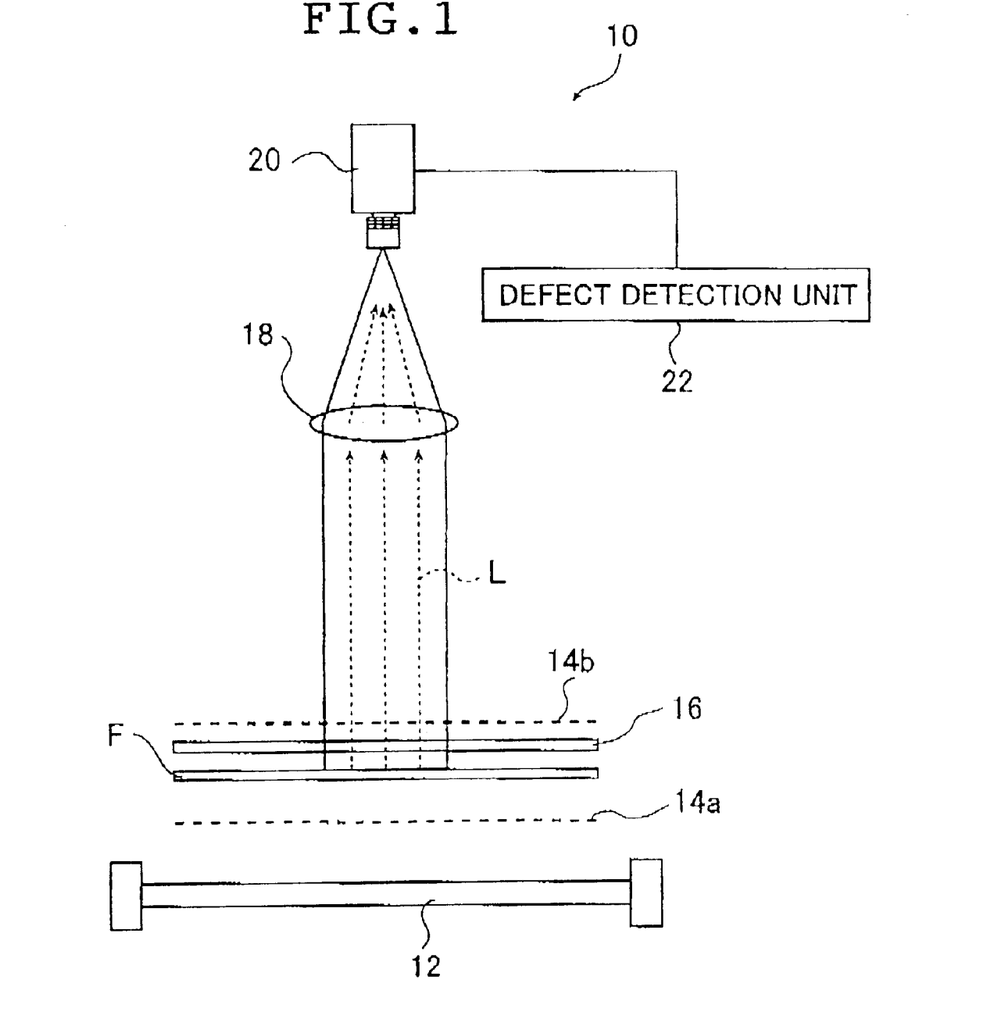
FIG. 1 is a diagram schematically showing the configuration of a film defect checking apparatus of the present invention.

FIG. 1 is a diagram schematically showing a film defect checking apparatus 10 for detecting defects in a viewing angle improving film in a preferred embodiment of a film defect checking apparatus of the present invention.

The film defect checking apparatus 10 is arranged to obtain a luminance signal for detecting optically defective portions of a viewing angle improving film (hereinafter referred to as "film") F, i.e., an apparatus for obtaining luminance signals for detecting defective portions differing in birefringent characteristics from the normal portion. The obtained luminance signal is sent to a defect detection unit 22 for detecting defects.

The film defect checking apparatus 10 has as its main components, an illumination light source 12, a pair of polarizers 14 consisting of a polarizer 14a and a polarizer 14b between which the film F is interposed from both sides, a liquid crystal correction film 16, an optical system 18, and a CCD camera 20.

The illumination light source 12 is a light source for uniformly projecting parallel rays onto the film surface of the film F through the polarizer 14a. For example, a transmission light is used as the illumination light source 12. Preferably, the projected light is white light. However, any light source may suffice if it can project light having a spectrum in the visible range. Also, the illumination light source 12 may be a surface illuminant capable of projecting light onto the surface of the film F so that a certain area thereof is uniformly illuminated, or a linear light source for projecting light onto the film surface of the film F so that the surface of the film F is uniformly projected along one direction.

The pair of polarizers 14 consists of the polarizer 14a and the polarizer 14b. The polarizer 14a is placed parallel to the surface of the film F. The polarizer 14a is an element for linearly polarizing or almost linearly polarizing light emitted from the illumination light source 12 before the light is incident upon the film F.

The polarizer 14b is placed parallel to the surface of the film F in the crossed-Nicols relationship with the polarizer 14a (with the polarizing transmission axis of the polarizer 14a and the polarizing transmission axis of the polarizer 14b set perpendicular to each other). The polarizer 14b is an element through which part of transmitted light L transmitted through the film F and the liquid crystal correction film 16 described below, i.e., the component of transmitted light L in the direction along the polarizing transmission axis of the polarizer 14b, is transmitted.

Well-known polarizers may be used as each of the polarizers 14a and 14b.

The optical system 18 is an optical system lens for converging transmitted light L, resulting in parallel rays being transmitted through the polarizer 14b, to effect imaging on the light receiving surface of the CCD camera 20. A well-known optical system lens may be used as the optical system 18. The reason for use of the optical system 18 for converging the transmitted light L in the form of parallel rays to effect imaging on the light receiving surface of the CCD camera 20 in this embodiment is because, if the optical system 18 is not used, a viewing angle dependence occurs in the luminance signal obtained from the quantity of transmitted light L received through the light receiving surface of the CCD camera 20, such that the value of the luminance signal varies depending upon the light receiving position on the light receiving surface of the CCD camera 20, thereby causing a viewing angle dependence. Thus, the optical system 18 is used as a viewing angle correction lens for obtaining a luminance signal without such a viewing angle dependence to eliminate the need for shading correction. On the other hand, the function of the liquid crystal correction film 16 described below reduces the viewing angle dependence so that the function makes it possible to obtain a luminance signal not requiring shading correction. Therefore, the optical system 18 is not always necessary. However, if there is a need for further reducing the viewing angle dependence and for detecting defective portions with higher accuracy, or if the value of the luminance signal is small and the signal-to-noise ratio is low, it is particularly preferable to use the optical system 18.

The CCD camera 20 is a light receiving means for receiving transmitted light L transmitted through the polarizer 14a, the film F, the liquid crystal correction film 16 and the polarizer 14b which is converged by the optical system 18, and for obtaining the luminance signal of transmitted light L. As this light receiving means, a line sensor is used which has solid-state image pickup elements arranged in a straight row on the light receiving surface. According to the present invention, solid-state image pickup elements on the light receiving surface may be two-dimensionally arrayed to form an area sensor. Also, according to the present invention, the CCD camera having solid-state image pickup elements on the light receiving surface is not exclusively used and any other well-known solid state image pickup device may be used, such as a complementary metal oxide semiconductor (CMOS) type image pickup device.

The liquid crystal correction film 16 is a component specific to the present invention and is provided such that a portion in a certain area of the film F which has been checked to confirm that it is free from any optical defect is cut out, rotated through 180° along a plane corresponding to the film surface, or reversed front side to back side, and placed parallel to the film F.

The following is the reason for using the liquid crystal correction film 16 having substantially the same birefringent characteristics as the film F after the rotation through 180° along a plane corresponding to the film surface or the reverse.

Namely, the film F is made so as to have predetermined birefringent characteristics. Therefore, if the liquid crystal correction film 16 is not placed in the film defect checking apparatus, the luminance signal obtained by the CCD camera 20 has a viewing angle dependence such as to be dependent on the light receiving position of the light receiving elements of the CCD camera 20, and the level of the luminance signal of the normal film portion is not uniform, so that the accuracy of detection of the defective portions from the luminance signal of the normal film surface is lowered. Therefore, the liquid crystal correction film 16 is used to correct the luminance signal so that the luminance signal of the normal film surface has a constant level independent of the light receiving position, in other words, the luminance signal is uniform in level.

Figure 2A:
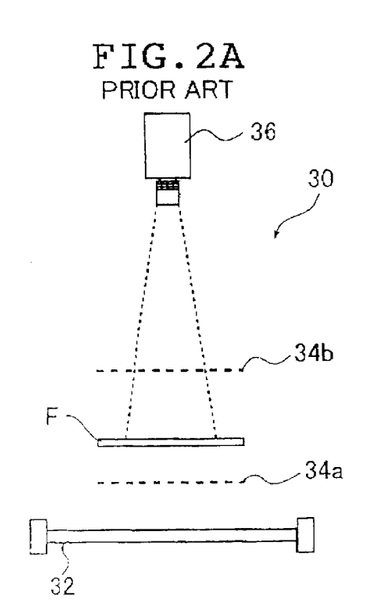
FIG. 2A is a diagram for explaining a conventional film defect checking apparatus.

For example, FIG. 2A shows an example of a conventional film defect checking apparatus 30 without liquid crystal correction film 16, which is of a type using no optical system 18.

Figure 2B:
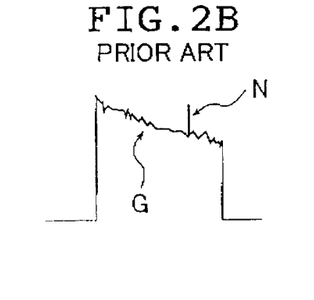
FIG. 2B is a diagram showing an example of a luminance signal obtained in the checking apparatus shown in FIG. 2A.

In the film defect checking apparatus 30, light emitted from an illumination light source 32 and transmitted through a polarizer 34a, a film F and a polarizer 34b is received by a CCD camera 36 having a line sensor forming a light receiving surface to obtain a luminance signal, which has a viewing angle dependence such that the level of a luminance signal G of the normal film surface exhibits an inclination in a rightward direction as viewed in FIG. 2B. Therefore, the signal-to-noise ratio of a luminance signal N of a defective portion superimposed on the normal luminance signal G is low, so that the defect detection accuracy is low.

Figure 2C:
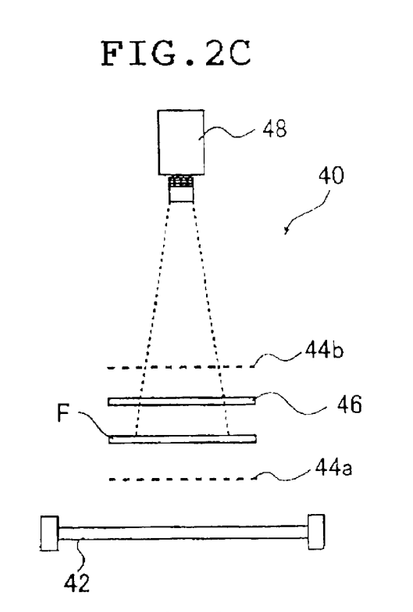
FIG. 2C is a diagram for explaining another example of the film defect checking apparatus of the present invention.

On the other hand (referencing FIG. 2C), film defect checking apparatus 40 being an example of the defect checking apparatus using liquid crystal correction film in accordance with the present invention, emits light from an illumination light source 42 and transmits said light through polarizer 44a, film F, liquid crystal correction film 46 (corresponding to liquid crystal correction film 16) and polarizer 44b, being received by CCD camera 48 having a line sensor forming a light receiving surface to obtain a luminance signal. This luminance signal is formed of a luminance signal N' of a defective portion and a luminance signal G' of the normal film portion on which luminance signal N' is superimposed, and which is made uniform (of course, containing noise components) by using the liquid crystal correction film 46 (see FIG. 2D). As a result, the defective portion can be detected from the luminance signal G' without performing shading correction.

Figure 2D:
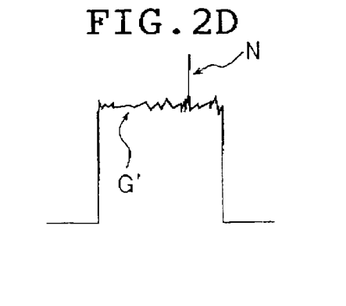
FIG. 2D is a diagram showing an example of a luminance signal obtained in the checking apparatus shown in FIG. 2C.

In the film defect checking apparatus 10, as described above, the luminance signal is uniform in level independent of the image pickup position, as shown in FIG. 2D, and can be obtained by using the liquid crystal correction film 16, so that the signal-to-noise ratio of the luminance signal of defective portions is improved and the quantity of transmitted light received by the CCD camera 20 is also increased to heighten the level of the luminance signal. Thus, the signal-to-noise ratio is improved, hence improving defect detection accuracy.

The liquid crystal correction film 16 having the above-described characteristics is formed such that the film F having no optical defect is placed after being rotated 180° along a plane corresponding to the film surface or reversed front side to back side. According to the present invention, however, any correction film other than the above-described liquid crystal correction film 16 may suffice for the correction in accordance with the present invention provided that the correction film has substantially the same birefringent characteristics as the film having no optical defects, and that its placement direction is previously set according to a predetermined birefringent characteristic of the film F so that the luminance signal obtained by the CCD camera 20 has no viewing angle dependence and is uniform in level.

The condition of having substantially the same birefringent characteristics is dependent on the extent of defects to be detected but may be represented by, for example, a condition that the difference between retardation values (the thickness×(the index of birefringence along a phase-delay axis–the index of birefringence along an axis perpendicular to the phase-delay axis)) is less than 30 nm, preferably 10 nm.

The liquid crystal correction film 16 may be adhered to the polarizer 14a or 14b. In the film defect checking apparatus 10, the liquid crystal correction film 16 is interposed between the film F and the polarizer 14b. However, the liquid crystal correction film 16 may alternatively be interposed between the polarizer 14a and the film F.

The defect detection unit 22 has predetermined emphasis circuits, e.g., a differentiation processing circuit, a spatial filter circuit or the like, and detection circuits corresponding to some kinds of defects, e.g., a "streak detection circuit" and a "thin smudge detection circuit". The luminance signal is processed by differentiation processing and filtering processing, these processes being performed in each detection circuit to ascertain the existence/nonexistence of a defect.

The solid-state image pickup elements are arranged in a row to form the CCD camera 20 of the film defect checking apparatus 10 as described above, and may be arranged in a left-right direction as viewed in FIG. 1, in a direction perpendicular to the plane corresponding to the drawing paper, or in a direction at a certain angle from the plane corresponding to the drawing paper.

If the film F is a long strip of film, and in a case it is checked by the film defect checking apparatus 10 while being conveyed, it is preferable that the solid-state image pickup elements of the CCD camera 20 be arranged along a line having an inclination with respect to a direction perpendicular to the direction of conveyance of the film F.

Figure 3:
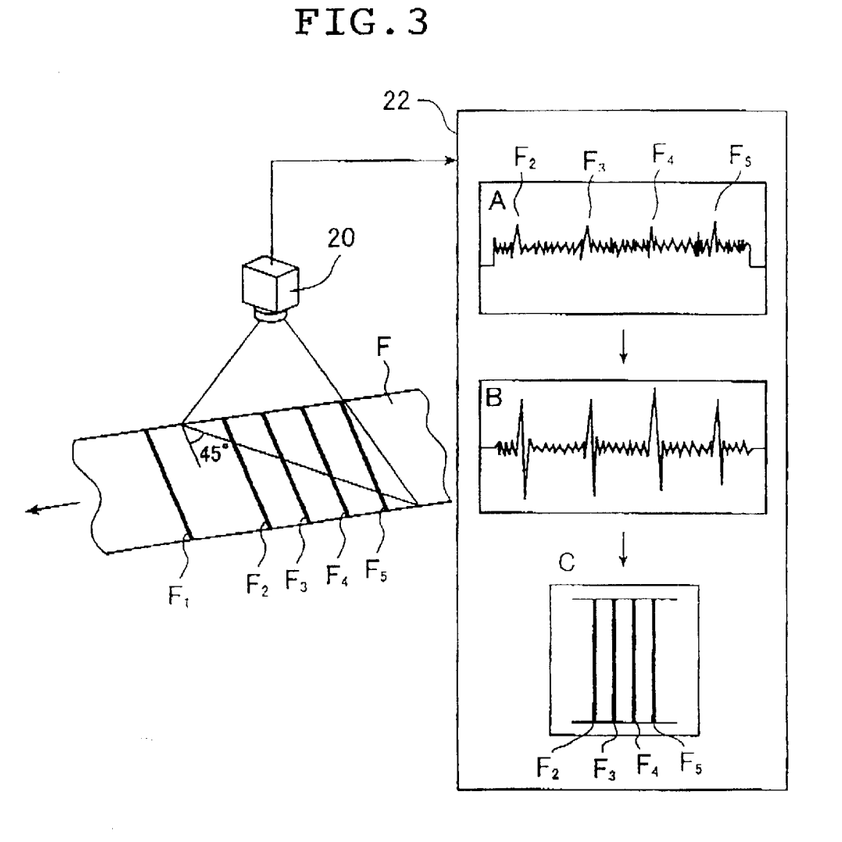
FIG. 3 is a diagram showing an example of the placement of light receiving means in the film defect checking apparatus of the present invention.

FIG. 3 shows an example of such an arrangement of the solid-state image pickup elements of the CCD camera 20. In FIG. 3, for ease of understanding, the relationship between the CCD camera 20 of the film defect checking apparatus 10 and the film F is shown in such a state that the illumination light source 12, the pair of polarizers 14, the correction film 16 and the optical system 18 are omitted.

In this example, the CCD camera 20 is a line sensor in which solid-state image pickup elements are arranged in a row, and is placed so as to be inclined at an angle of 45° from a line perpendicular to the direction of conveyance of the film F. That is, the solid-state image pickup elements of the CCD camera 20 are arranged in a row inclined at an angle of 45° from a line perpendicular to the direction of conveyance of the film F. The effect of this placement of the CCD camera 20 is as described below. Even with respect to a stepped nonuniformity which has occurred in a direction perpendicular to the direction of conveyance of the film F as indicated by $F_1$ to $F_5$ due to a nonuniform thickness of application of a liquid crystal to the surface of a flexible supporting member during the process of manufacturing the film F, luminance signal A (see FIG. 3) supplied to defect detection unit 22 has luminance signal value variations corresponding to the stepped nonuniformity regions $F_1$ to $F_5$. The defect detection unit 22 differentiates this luminance signal A in the differentiation processing circuit to determine variations in the luminance signal, thereby obtaining a differentiated luminance signal B. The defect is thereby emphasized and can be easily detected from a comparison between the signal value of the differentiated luminance signal B and a threshold value. The luminance signal A or the differentiated luminance signal B processed as described above, undergoes image rotation processing such that the direction of conveyance of the film F is indicated horizontally or vertically on a screen to enable display of an image C on the monitor.

Figure 4:
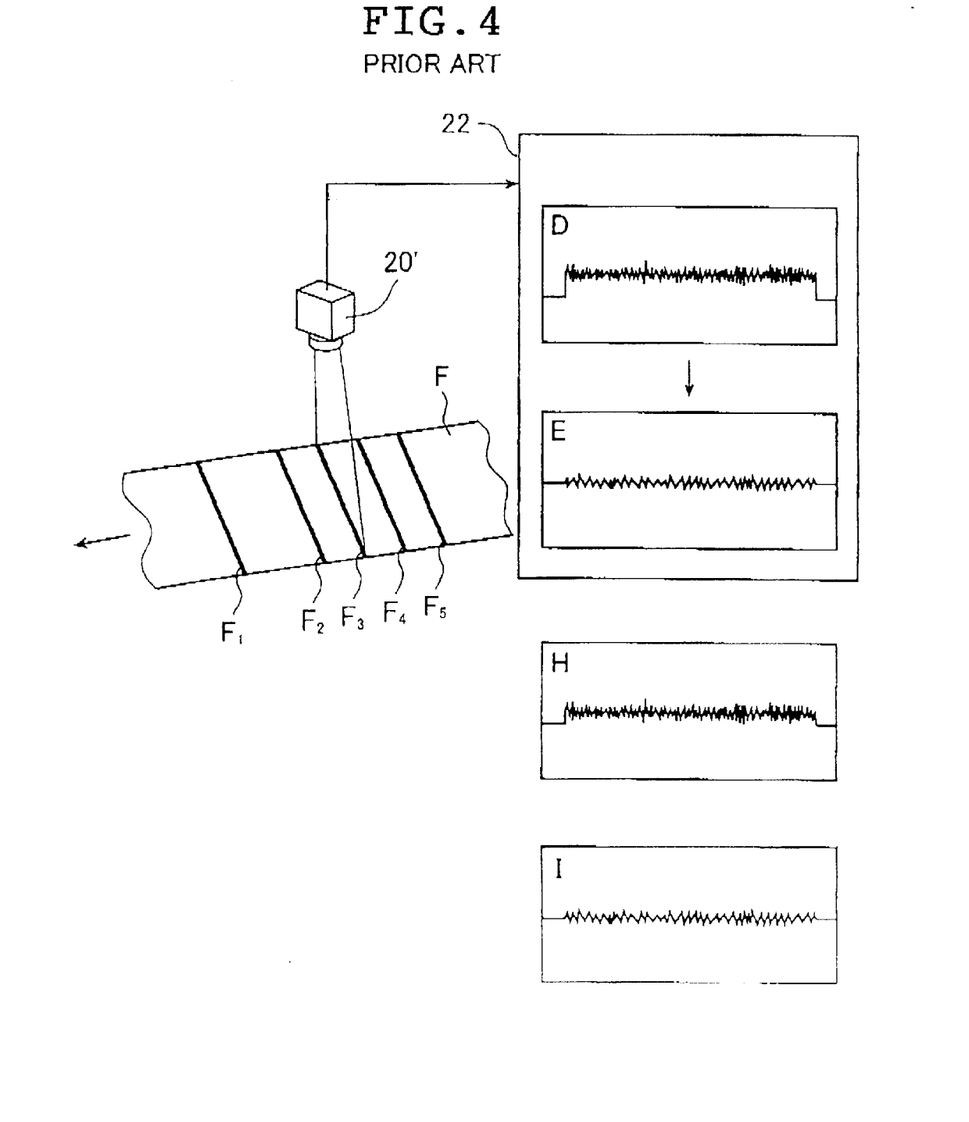
FIG. 4 is a diagram showing an example of the placement of light receiving means in the conventional film defect checking apparatus.

On the other hand, in a case where, as shown in FIG. 4, solid-state image pickup elements of a CCD camera 20' are arranged in a direction perpendicular to the direction of conveyance of the film F, a luminance signal D obtained by imaging a stepped nonuniformity $F_3$ has only a change in DC component level in comparison with a luminance signal H of the normal portion having no stepped nonuniformity (see FIG. 4). Therefore, a differentiated luminance signal E obtained by differentiation processing has substantially no large variation in luminance signal value, as does a differentiated luminance signal I of the normal portion having no defect. As a result, the defect cannot be detected from a comparison between the luminance signal value and a threshold value.

Thus, it is preferable to set the placement direction of the CCD camera 20 by presupposing a direction of a defect occurrence such as a stepped nonuniformity liable to have a unidirectional distribution.

In the example shown in FIG. 3, the direction of arrangement of the solid-state image pickup elements is inclined at an angle of 45° from a line perpendicular to the direction of conveyance of the film F. According to the present invention, the inclination angle is not limited to this value. However, it is preferable to set the inclination angle to 45° by considering the case of image display in which the direction of conveyance is indicated horizontally or vertically on the monitor screen (not shown), and the facility with which image rotation processing is performed.

The film defect checking apparatus 10 and the defect detection unit 22 are arranged as described above.

In the thus-arranged film defect checking apparatus 10, only a component linearly polarized in one direction in light uniformly emitted from the illumination light source 12 passes through the polarizer 14a to be incident upon the film F. The linearly polarized light is transmitted through the film F while being elliptically polarized according to the birefringent characteristics of the film F. The light emergent from the film F is transmitted through the liquid crystal correction film 16 while being further polarized elliptically according to the birefringent characteristics of the liquid crystal correction film 16. Of the elliptically polarized light transmitted through the liquid crystal correction film 16, only the component along the polarizing transmission axis of the polarizer 14b placed in the crossed-Nicols relationship with the polarizer 14a is transmitted through the polarizer 14b, converged by the optical system 18 and received by the CCD camera 20.

If the film F has a defect, the elliptical polarized components of the light passing through the defective portion are different from those of the light passing through the normal portion having no defect. Therefore, the luminance signal obtained by the CCD camera 20 receiving the light has a large change in its luminance signal value corresponding to the defective portion. For example, the luminance signal value is increased.

On the other hand, the luminance signal obtained by the CCD camera 20 is made uniform independent of the viewing angle by the effect of the liquid crystal correction film 16. According to the present invention, light elliptically polarized according to the birefringent characteristics of the film F is not returned to the linearly polarized state according to the birefringent characteristics of the liquid crystal correction film 16. In other words, the anisotropy of the birefringence index of the film F is not compensated by using the anisotropy of the birefringence index of the liquid crystal correction film 16. That is, according to the present invention, the viewing angle dependence of the CCD camera due to the birefringent characteristics of the film F, e.g., the viewing angle dependence that resides in the change in the luminance signal value according to the light receiving position of the light receiving elements, is corrected by utilizing the birefringent characteristics of the liquid crystal correction film 16, thereby uniformly maintaining the luminance signal at a certain level.

The luminance signal thus obtained is sent to the defect detection unit 22, undergoes differentiation processing and spatial filter processing, and is supplied to various circuits for detecting luminance signals corresponding to defective portions from the uniform-level luminance signal by discriminating the defective portion signals from noise components, thus detecting defects from the luminance signal.

As described above, the film defect checking apparatus of the present invention uses a liquid crystal correction film to obtain a uniform-level luminance signal having substantially no viewing angle dependence. This film defect checking apparatus can be used in the process of manufacturing the film (liquid crystal viewing angle improving film) F to accurately detect, without any fail, all optical defects caused in the process of manufacturing the film F. A defect check system of the present invention in which the film defect checking apparatus of the present invention is applied to the process of manufacturing the film F will now be described.

Figure 5:
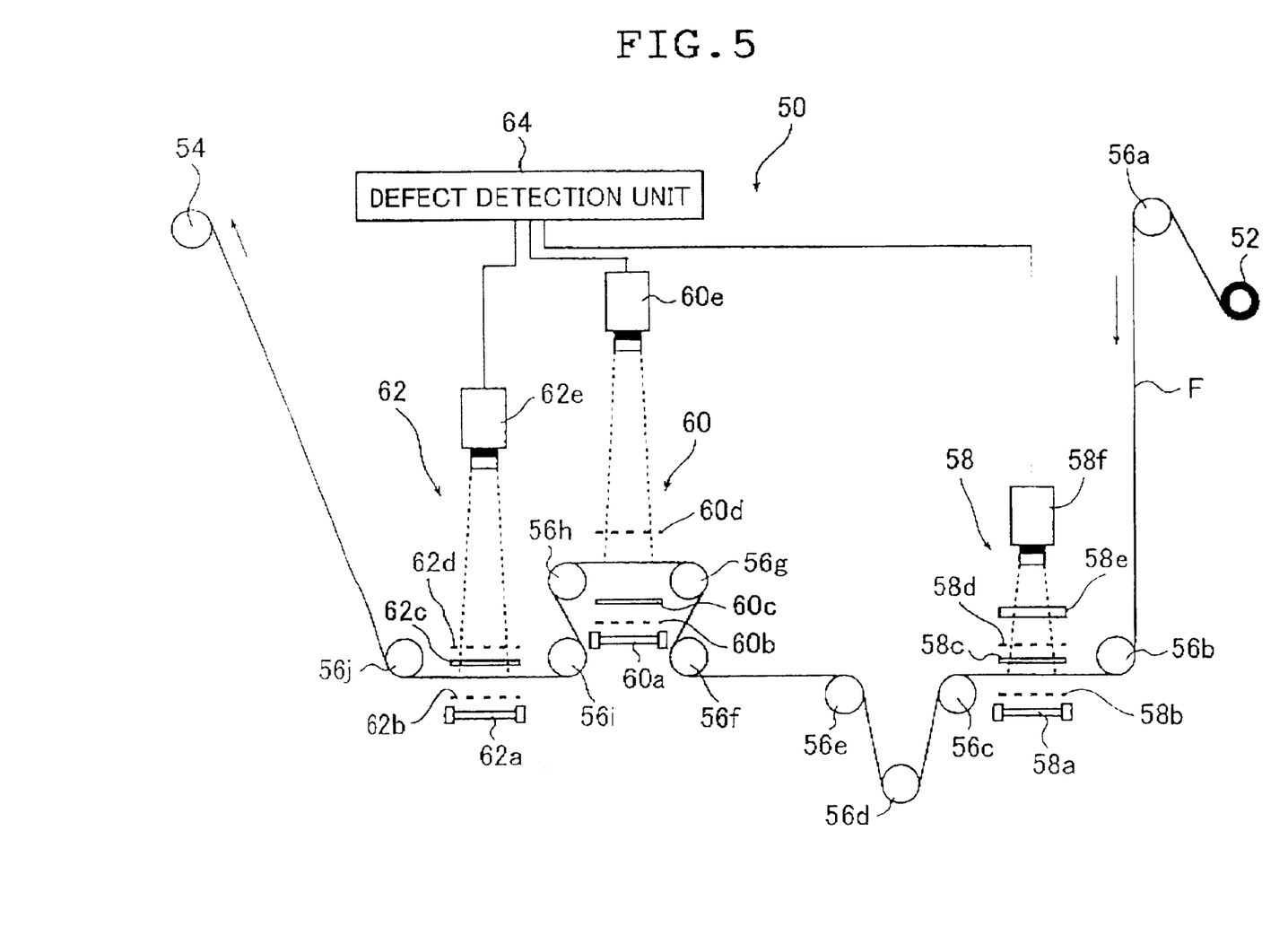
FIG. 5 is a diagram schematically showing the configuration of a film defect check system of the present invention.

FIG. 5 shows, as an example of the defect check system of the present invention, a defect check system 50 for checking the film F for defects in a liquid crystal viewing angle improving film F.

The defect check system 50 has film defect checking apparatuses 58, 60, and 62, each constructed as the film defect checking apparatus in accordance with the present invention, and a defect detection unit 64. The film F to be checked is manufactured by various steps, including the steps of applying a liquid crystal to the surface of a flexible supporting member, drying the liquid crystal, orienting the liquid crystal and hardening the liquid crystal film.

In the defect check system 50, the manufactured film F is in a state of being rolled around a take-up roll 52 and is continuously unrolled and conveyed from the take-up roll 52 by rollers 56a to 56j to be finally wound around a take-up roll 54. The film defect checking apparatuses 58, 60, and 62 are disposed along the path of this conveyance, and respectively obtain luminance signals and supply the luminance signals to the defect detection unit 64 for detection of defects.

The defect detection unit 64, like the defect detection unit 22, has a differentiation processing circuit, a spatial filter circuit, and detection circuits corresponding to some kinds of defects, e.g., a "streak detection circuit" and a "thin smudge detection circuit." The defect detection unit 64 processes each of the luminance signals supplied from the film defect checking apparatuses 58, 60, and 62 in the differentiation processing circuit and the spatial filter circuit, and ascertains the existence/nonexistence of defects in the detection circuits, thereby detecting defects.

The film defect checking apparatus 58 has an illumination light source 58a, a polarizer 58b, a liquid crystal correction film 58c, a polarizer 58d, an optical system 58e, and a CCD camera 58f. These components correspond to the illumination light source 12, the polarizer 14a, the liquid crystal correction film 16, the polarizer 14b, the optical system 18, and the CCD camera 20 of the above-described film defect checking apparatus 10, and have the same constructions and functions as those described above. Therefore, the description for these components will not be repeated.

The polarizers 58b and 58d have their polarizing transmission axes set in the crossed-Nicols relationship with each other, and one of the polarizing transmission axes of the polarizers 58b and 58d is set parallel to the direction of conveyance of the film F. That is, the angle of intersection of the polarizing transmission axis of one of the pair of polarizers with respect to the direction of conveyance (whereby the angle of intersection is referred to as an angle at which the polarizing transmission axis of one of the pair of polarizers intersects the direction of conveyance) is set to a degree of approximately zero. This angle of approximately zero is, for example, within a range of 2 to 3 degrees, although the tolerance range thereof varies depending upon the birefringent characteristics of the film F.

The film defect checking apparatus 60 has an illumination light source 60a, a polarizer 60b, a liquid crystal correction film 60c, a polarizer 60d, and a CCD camera 60e. These components correspond to the illumination light source 12, the polarizer 14a, the liquid crystal correction film 16, the polarizer 14b, and the CCD camera 20 of the above-described film defect checking apparatus 10, and have the same constructions and functions as those described above. Therefore, the description for these components will not be repeated.

The film defect checking apparatus 60 includes no optical system corresponding to the optical system 18. The polarizers 60b and 60d have their polarizing transmission axes set in the crossed-Nicols relationship with each other, and one of the polarizing transmission axes of the polarizers 60b and 60d is slightly inclined relative to the direction of conveyance. For example, it is set by being inclined at an angle in the range of 5 to 15 degrees. That is, the angle of intersection of a polarizing transmission axis of the pair of polarizers with the direction of conveyance is set to, for example, 5 to 15 degrees, preferably about 10 degrees.

The film defect checking apparatus 62 has an illumination light source 62a, a polarizer 62b, a liquid crystal correction film 62c, a polarizer 62d, and a CCD camera 62e. These components correspond to the illumination light source 12, the polarizer 14a, the liquid crystal correction film 16, the polarizer 14b, and the CCD camera 20 of the above-described film defect checking apparatus 10, and have the same constructions and functions as those described above. Therefore, the description for these components will not be repeated.

The film defect checking apparatus 62 includes no optical system corresponding to the optical system 18. The polarizers 62b and 62d have their polarizing transmission axes set in the crossed-Nicols relationship with each other, and one of the polarizing transmission axes of the polarizers 62b and 62d is set by being inclined at an angle about 45 degrees, for example, at an angle in the range of 35 to 45 degrees from the direction of conveyance. That is, the angle of intersection of the polarizing transmission axes of the pair of polarizers with the direction of conveyance is set to, for example, 35 to 45 degrees, preferably about 45 degrees.

The angles of intersection of the polarizing transmission axes of the polarizers in the film defect checking apparatuses 58, 60, and 62 are varied as described above in order to obtain the luminance signal in such a state that the signal-to-noise ratio is maximized according to the kinds and extents of defects in the film F. The function of this system relating to this effect will be described below.

Figure 6:
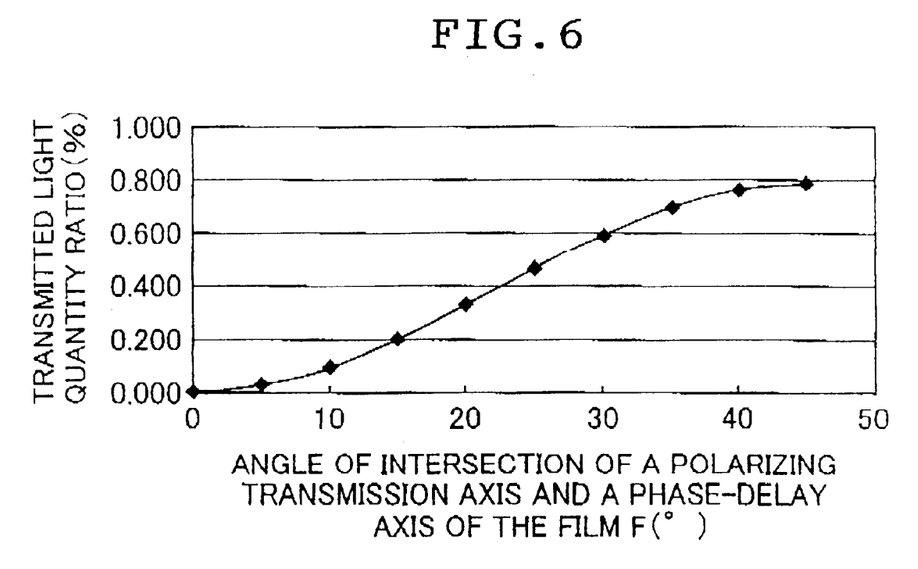
FIG. 6 is a diagram showing a characteristic represented by the transmitted light quantity ratio obtained by the film defect checking apparatus of the present invention.

FIG. 6 shows changes in the ratio of the quantity of light transmitted through and emergent from one of the pair of polarizers 14 in the film defect checking apparatus 10 to the quantity of light incident upon the other polarizer 14 (transmitted light quantity ratio) with respect to the angle of intersection of the polarizing transmission axis of one of the pair of polarizers 14 and the phase-delay axis of the film F when the retardation value of the film F (the thickness of the film F×(the index of birefringence along the phase-delay axis—the index of birefringence along an axis perpendicular to the phase-delay axis)) is 22 nm.

As can be understood from FIG. 6, in a case where the angle of intersection of the phase-delay axis of the film F and the polarizing transmission axis is zero, that is, the phase-delay axis of the film F and the polarizing transmission axis of one of the polarizers are parallel to each other, light incident upon the film F is transmitted through the film F without being changed from the state of being linearly polarized by the polarizer 14a and is, therefore, not transmitted through the polarizer 14b placed in the crossed-Nicols relationship. Thus, the transmitted light quantity ratio is zero. As the angle of intersection of the phase-delay axis of the film F and the polarizing transmission axis is increased, the influence of the birefringent characteristics of the film F on the light linearly polarized by the polarizer 14a becomes greater, so that the elliptically polarized components of the light become stronger. Accordingly, the quantity of light transmitted through the polarizer 14b increases gradually with the increase in the intersection angle, so that the transmitted light quantity ratio becomes higher.

A case where a defect exists in the film F, that is, the direction of the phase-delay axis of the film F is disordered to cause a change in the angle of intersection between the phase-delay axis and the polarizing transmission axis, will now be considered. For example, if the defect in the film F is such a large orientational defect that the phase-delay axis is inclined through an angle equal to or larger than a predetermined value, e.g., 5 degrees or more by the orientational defect in the liquid crystal, the direction of the phase-delay axis at the portion having the large orientational defect is largely changed to considerably increase the intersection angle from the polarizing transmission axis even when the angle of intersection of the phase-delay axis of the normal portion of the film F and the polarizing transmission axis is zero, so that the quantity of transmitted light is largely changed in correspondence with the intersection angle shown in FIGS. 6. As a result, a luminance signal obtained from the defective portion is detected as a large change in the signal level.

On the other hand, in a case where the phase-delay axis of an orientational defect is inclined relative to the polarizing transmission axis of the polarizer 14 but the orientational defect is so small that inclination angle is smaller than a predetermined angle, e.g., smaller than 5 degrees, it is difficult to detect the small orientational defect as a luminance signal when the angle of intersection of the phase-delay axis of the normal portion of the film F and the polarizing transmission axis is about zero, because, as shown in FIG. 6, the transmitted light quantity ratio is not sufficiently changed with respect to a small change in the intersection angle in the vicinity of the zero intersection angle. In such a situation, the angle of intersection of the phase-delay axis of the film F and the polarizing transmission axis may be set to 5 to 15 degrees, e.g., 10 degrees to amplify the change in the transmitted light quantity ratio corresponding to a small change in the direction of the phase-delay axis. That is, with respect to a small orientational defect, the angle of intersection of the phase-delay axis of the normal film F and the polarizing transmission axis of the polarizer 14 is set to 5 to 15 degrees to increase the change in the transmitted light quantity ratio due to the small orientational defect, thereby amplifying the change in the luminance signal. Thus, the signal-to-noise ratio is increased to improve the accuracy with which defects are detected.

In this embodiment, the above-described intersection angle is limited within the range of 5 to 15 degrees to effectively detect the luminance signal of small orientational defects while limiting the luminance signal of the normal portion of the film F to a small level. According to the present invention, it is not necessary to limit the above-described intersection angle to 5 to 15 degrees in accordance with some birefringent characteristics of the film F. The intersection angle may be suitably set according to the relationship between the transmitted light quantity ratio and the intersection angle as represented by a curve in FIG. 6.

A different situation will also be considered where the film F has no orientational defect but there is a phase-difference defect such that the retardation value varies due to an application nonuniformity or the like in the manufacturing process, i.e., the above-described stepped nonuniformity.

When the angle of intersection of the phase-delay axis and the polarizing transmission axis of the polarizer 14 (referencing FIG. 6) is small, the transmitted light quantity ratio is naturally low and, therefore, it does not change largely with respect to a change in the retardation value due to the above-described phase-difference defect. On the other hand, when the above-described intersection angle is large, the transmitted light quantity itself is large and, therefore, the change in the transmitted light quantity ratio with respect to the retardation value is large (referencing FIG. 7), as seen by the change in the transmitted light quantity ratio with respect to the retardation value when the above-described intersection angle is 45 degrees.

Figure 7:
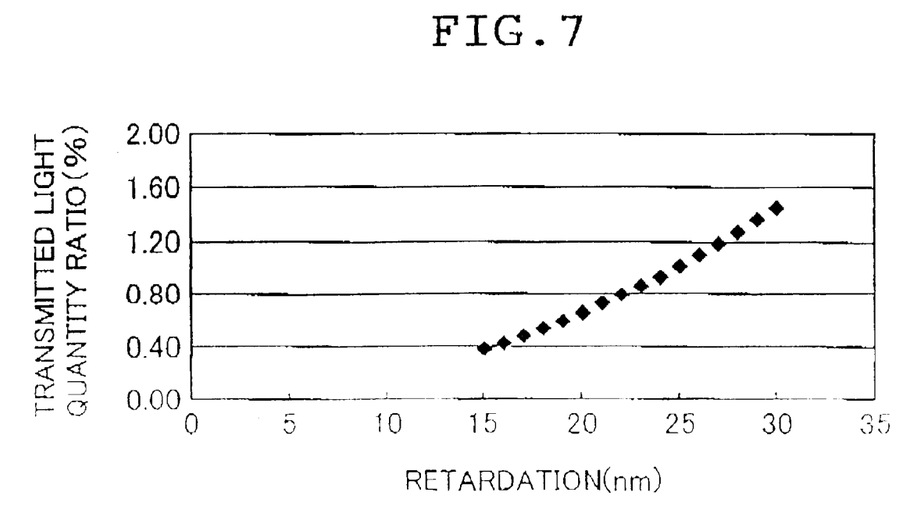
FIG. 7 is a diagram showing another characteristic represented by the transmitted light quantity ratio obtained by the film defect checking apparatus of the present invention.

In the case of a phase-difference defect corresponding to a change in the retardation value, therefore, the above-described intersection angle may be set to a large value, for example, 35 to 45 degrees, preferably 45 degrees so that the transmitted light quantity ratio can be changed largely with respect to the change in the retardation value. The change in the luminance signal of the phase-difference defect portion is thereby amplified to improve the signal-to-noise ratio and, hence, the accuracy with which the phase-difference defect is detected can be improved. As mentioned above, it is preferred that the intersection angle be 45 degrees. This is because, since the polarizers 14 are placed in the crossed-Nicols relationship with each other, the transmitted light quantity ratio is maximized at the intersection angle of 45 degrees and the change in the transmitted light quantity ratio with respect to the retardation value is maximized at this intersection angle.

According to the present invention, it is not necessary to limit the intersection angle to 35 to 45 degrees in accordance with some birefringent characteristics of the film F. The intersection angle may be suitably set according to the relationship between the transmitted light quantity ratio and the intersection angle as represented by the curve in FIG. 6.

As described above, it is possible to accurately detect defects without any fail by changing the angle of intersection of the phase-delay axis of the normal portion of the film F and the polarizing transmission axis of the polarizers in accordance with the kinds and extent of the defects.

In the film defect check system 50, the polarizing transmission axis of the polarizers in each of the film defect checking apparatuses 58, 60, and 62 is changed in a predetermined direction relative to the direction of conveyance of the film F on the basis of the above-described principle and by utilizing the condition of the conveyed film F having its phase-delay axis formed in a direction perpendicular to the direction of conveyance when manufactured.

That is, in the film defect checking apparatus 58, for the purpose of accurately detecting a large orientational defect, one polarizing transmission axis of the polarizer 58b or 58d is set to an angle of about zero degree from the direction of conveyance, that is, approximately parallel to the direction of conveyance to set the angle of intersection of the phase-delay axis of the film F and the polarizing transmission axis of the polarizer 58b or 58d to about zero degree, that is, to set the phase-delay axis and the polarizing transmission axis approximately parallel to each other.

Under this condition, the film defect checking apparatus 58 can obtain such a luminance signal as to detect a large orientational defect with improved accuracy, and can also obtain such a luminance signal as to accurately detect defects due to mixing of foreign materials, which variously change the direction of the phase-delay axis as well as the retardation value.

In the film defect checking apparatus 60, for the purpose of accurately detecting a small orientational defect, the angle of intersection of the phase-delay axis of the film F and one polarizing transmission axis of the polarizer 60b or 60d is set to about 10 degrees and, accordingly, the other polarizing transmission axis of the polarizer 60b or 60d is set at an angle of about 10 degrees from the direction of conveyance. Under this condition, the defect checking apparatus 60 can obtain such a luminance signal as to detect a small orientational defect with improved accuracy, and can also obtain such a luminance signal as to accurately detect large orientational defects as well as defects due to mixing of foreign materials, any of which variously change the direction of the phase-delay axis and, hence, the retardation value.

In the film defect checking apparatus 62, for the purpose of accurately detecting a phase-difference defect corresponding to a change in retardation value other than orientational defects corresponding to changes in the direction of the phase-delay axis, the angle of intersection of the phase-delay axis of the film F and one polarizing transmission axis of the polarizer 62b or 62d is set to about 45 degrees and, accordingly, the other polarizing transmission axis of the polarizer 62b or 62d is set at an angle of about 45 degrees from the direction of conveyance. Under this condition, the defect checking apparatus 62 can obtain such a luminance signal as to detect a phase-difference defect with improved accuracy.

Thus, the defect check system 50 is arranged to detect orientational defects in optical defects in the film F, corresponding to changes in the direction of the phase-delay axis, by sorting them into large and small orientational defects according to their extent of defectiveness, and to also detect phase-difference defects corresponding to changes in retardation value as well as defects, due to mixing of foreign materials.

In the defect check system 50, three defect checking apparatuses are disposed with the polarizing transmission axes of the pairs of polarizers respectively intersecting the direction of conveyance at angles of about zero, about 10 degrees, and about 45 degrees. In the defect check system 50 of the present invention, however, each of the number of defect checking apparatuses and their respective angles of intersection can be set without limitation, and the above-described intersection angle may be variously changed according to the direction of the phase-delay axis of the film F and the birefringent characteristics represented by the retardation value.

Figure 8:
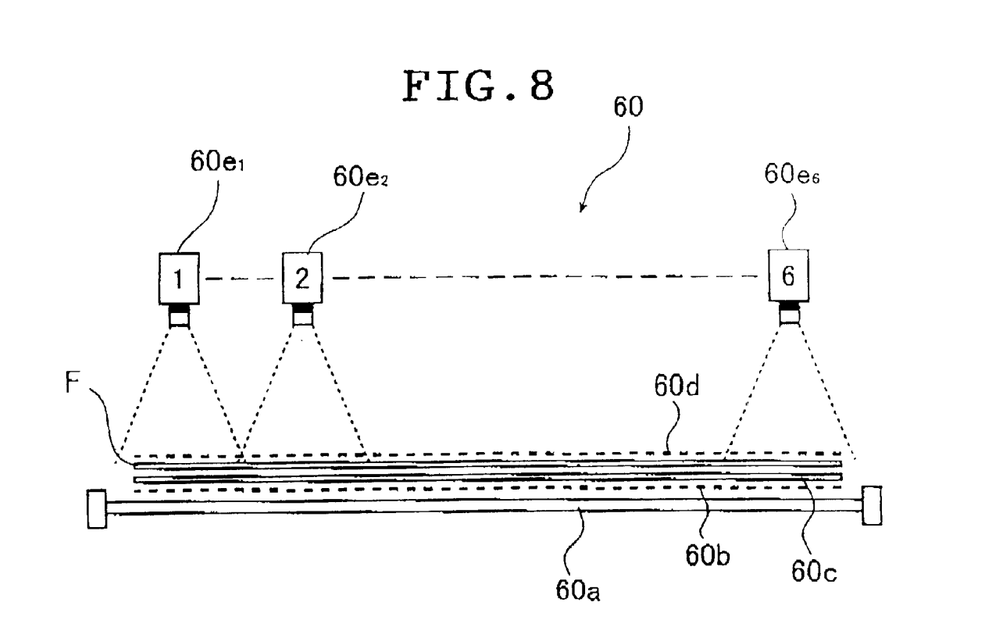
FIG. 8 is a diagram schematically showing an example of film defect checking apparatuses used in the defect check system of the present invention.

In the film defect checking apparatuses 58, 60, and 62 of the film defect check system 50, a plurality of CCD cameras are disposed so as to fully cover the film F in the width direction thereof. For example, in the film defect checking apparatus 60, as shown in FIG. 8, a CCD camera assembly 60e consisting of CCD cameras $60e_1$ to $60e_6$ arranged in correspondence with the width of the film F receives transmitted light ranging through the entire width of the film F continuously conveyed and sends a luminance signal to the defect detection unit 64.

In the above-described defect check system 50, the film F is continuously conveyed at a speed of, for example, 18 m per minute; six CCD cameras are arranged in the width-wise direction of the above-described manner; the resolution of the camera system is set to, for example, 0.125 mm; the luminance signal obtained by the film defect checking apparatus 60 is processed in the differentiation circuit, the spatial filter circuit, and the "thin smudge detection circuit"; and the luminance signal obtained by the film defect checking apparatus 60 is processed in the differentiation circuit, the spatial filter circuit, and the "streak detection circuit", thus performing the film check for defects in an in-line process.

In particular, the above-described application nonuniformity in the process of manufacturing the film F appears as a stepped nonuniformity parallel to a line perpendicular to the direction of conveyance and causes a phase-difference defect characterized by a change in retardation value. Preferably, if such a stepped nonuniformity is detected by using the film defect checking apparatus 62 having the polarizer 62b or 62d with the polarizing transmission axis inclined at an angle of about 45 degrees from the direction of conveyance, the CCD camera 62e or a plurality of CCD cameras, e.g., six CCD cameras used in correspondence with the width of the film F as described above to perform the image pickup operation in a state of being inclined relative to the direction perpendicular to the direction of conveyance of the film F, such as at an angle of 45 degrees from this direction. Preferably, when this image pickup operation is performed, image rotation processing is performed in the defect detection unit 64 such that the direction of conveyance is indicated along the horizontal or vertical direction on the monitor screen, thus enabling quantification of the generation cycle and the intensity of a stepped nonuniformity in the process of manufacturing the film F.

The apparatus, system and method for film checking defects in a film in accordance with the present invention have been described in detail. Needless to say, the present invention is not limited to the above-described embodiments, and various modifications and changes of the described embodiments may be made without departing from the scope of the present invention.

As described above in detail, a correction film which has substantially the same birefringent characteristics as a film in a state of having no optical defects, and whose position is previously set in a certain direction according to the birefringent characteristics of the film is employed to make the level of the luminance signal constant and to increase the quantity of transmitted light. The signal-to-noise ratio of the luminance signal corresponding to a defective portion is thereby increased, so that the defect detection accuracy is improved. This method enables a simpler and easier check of a film for optical defect in a manufacturing line or the like.

Further, the direction of the polarizing transmission axes of the pair of polarizers may be changed to accurately detect, without any fail, all optical defects caused in a manufacturing process. In particular, in the process of manufacturing a viewing angle improving film for use in a liquid crystal display device or the like, detection of defects due to mixing of a foreign material, an orientation nonuniformity, a stepped nonuniformity, and the like, can be performed continuously without any fail. This method is effective in-line inspection of all the film in a manufacturing process. In particular, a stepped nonuniformity can be detected based on the luminance signal value of the luminance signal and, therefore, the generation cycle and the intensity of the stepped nonuniformity can be quantified by performing differentiation processing and image processing.

What is claimed is:

1. An apparatus for checking a film for optical defects, comprising:

a pair of polarizers placed on opposite sides of a film surface of a film to be checked with respect to said optical defects, said polarizers being parallel to the film;

an illumination light source placed outside said pair of polarizers, said illumination light source projecting light onto the film through a first polarizer of said pair of polarizers;

a light receiving unit placed outside said pair of polarizers and opposite from a fixed position of said illumination light source, said light receiving unit receiving light transmitted through a second polarizer of said polarizers; and a correction film having substantially birefringent characteristics identical to birefringent characteristics of a portion of the film having no optical defects, a direction in which said correction film is to be positioned being previously set according to the birefringent characteristics of the film, said correction film being placed in one of two spaces between said pair of polarizers and the film parallel to the film, wherein a luminance signal of light transmitted through the film, said correction film and said pair of polarizers is obtained by said light receiving unit to check the film for optical defects.

2. The apparatus according to claim 1, wherein a portion of the film having no optical defects is placed as said correction film after being rotated through 180 degrees along a plane corresponding to the film surface or after being reversed from front side to back side.

3. The apparatus according to claim 1, wherein said correction film is adhered to one of said pair of polarizers.

4. The apparatus according to claim 1, further comprising an optical system for converging transmitted light on said light receiving unit, said optical system being provided in an optical path for the transmitted light between said light receiving unit and the second polarizer.

5. The apparatus according to claim 1, wherein said light receiving unit comprises solid-state image pickup elements.

6. The apparatus according to claim 5, wherein, when the film is checked for optical defects during conveyance of the film, said light receiving unit comprises a plurality of solid-state image pickup elements arranged in a row inclined relative to a direction perpendicular to a direction of conveyance of the film.

7. The apparatus according to claim 1, wherein the pair of polarizers are placed in crossed-Nicols relationship with each other.

8. A film defect check system for checking a film continuously conveyed for optical defects, said system comprising a plurality of film defect checking apparatuses placed in a path through which the film is conveyed, each of said film defect checking apparatuses having:

a pair of polarizers placed on opposite sides of a film surface of the film to be checked with respect to said optical defects, said polarizers being parallel to the film;

an illumination light source placed outside said pair of polarizers, said illumination light source projecting light onto the film through a first polarizer of said pair of polarizers;

light receiving unit placed outside said pair of polarizers and opposite from a placed position of said illumination light source, said light receiving unit receiving light transmitted through a second polarizer of said polarizers; and a correction film having substantially birefringent characteristics identical to birefringent characteristics of a portion of the film having no optical defects, a direction in which said correction film is to be positioned being previously set according to the birefringent characteristics of the film, said correction film being placed in one of two spaces between said pair of polarizers and the film parallel to the film, wherein directions of polarizing transmission axes of said pairs of polarizers of said plurality of film defect checking apparatuses are respectively set at different angles from a direction of conveyance of the film continuously conveyed.

9. The system according to claim 8, wherein a number of said film defect checking apparatuses is at least three, and said pairs of polarizers of said at least three film defect checking apparatuses are placed so that angles each of which is an angle of intersection of a polarizing transmission axis of one of said pair of polarizers in each of film defect checking apparatuses and a phase-delay axis of a portion of the film having no optical defects include an angle of about zero, an angle in a range of 5 to 15 degrees, and an angle in a range of 35 to 45 degrees.

10. The system according to claim 8, wherein, in at least one of said film defect checking apparatuses, said light receiving unit comprises a plurality of solid-state image pickup elements arranged in a row inclined relative to a direction perpendicular to the direction of conveyance of the film.

11. The system according to claim 8, wherein the pair of polarizer is placed in crossed-Nicols relationship with each other.

12. A method of checking a film for defects, in which a film interposed between a pair of polarizers parallel to each of the pair of polarizers is checked for optical defects by projecting illumination light from outside of a first polarizer of the pair of polarizers, and by receiving light transmitted through a second polarizer of the pair of polarizers, said method comprising the steps of:

placing a correction film which has substantially birefringent characteristics identical to birefringent characteristics of a portion of the film having no optical defects in one of two spaces between the pair of polarizers and the film parallel to a film surface of the film, a direction in which said correction film is to be positioned being previously set according to the birefringent characteristics of the film; and projecting the illumination light to the first polarizer.

13. The method according to claim 12, wherein directions of polarizing transmission axes of the pair of polarizers are set according to each of kinds of defects in the film, the pair of polarizers keeping crossed-Nicols relationship with each other.

* * * * *